Figure 1:
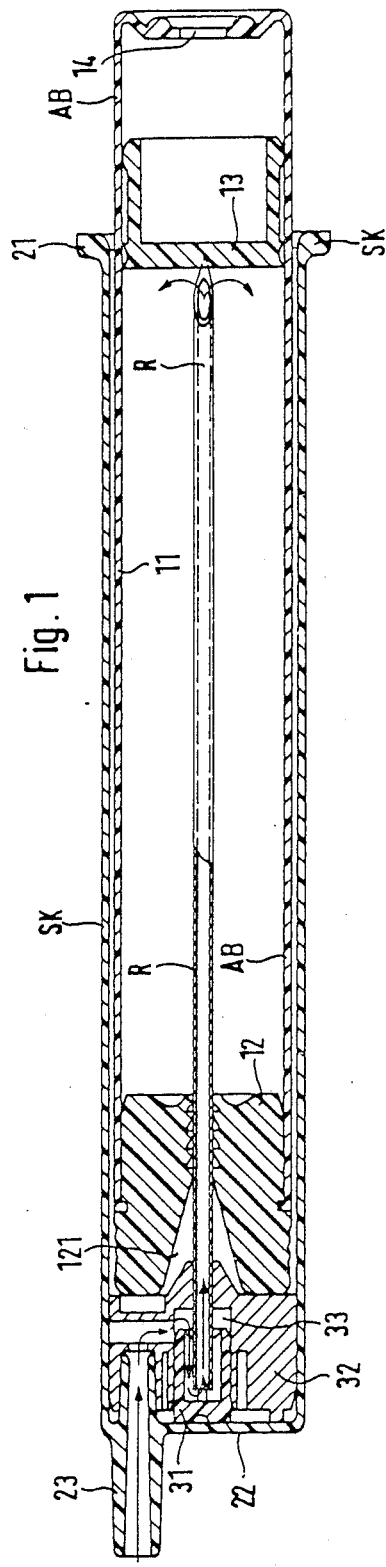

United States Patent [19]

Schwöbel et al.

[11] Patent Number: 4,790,330
[45] Date of Patent: Dec. 13, 1988

[54] BLOOD WITHDRAWAL DEVICE WITH SAFETY VALVE AND CYLINDRICAL CONTAINER

[75] Inventors: Eckhard Schwöbel, Lucerne; Hubert Bäumle, Escholzmatt, both of Switzerland

[73] Assignee: Intermedicat GmbH, Emmenbrucke, Switzerland

[21] Appl. No.: 930,349

[22] Filed: Nov. 12, 1986

[30] Foreign Application Priority Data

Nov. 30, 1985 [EP] European Pat. Off. .......... 85115241

[51] Int. Cl.⁴ ............................................. A61R 5/00
[52] U.S. Cl. ..................... 128/764; 604/52; 604/414
[58] Field of Search .............. 604/51, 52, 187, 256, 604/264, 272, 403, 411, 414, 415; 128/763, 764, 765, 766, 770

[56] References Cited

U.S. PATENT DOCUMENTS

| | | |
|---|---|---|
| 3,159,159 | 12/1964 | Cohen . |
| 3,494,352 | 2/1970 | Russo et al. ............ 128/764 |
| 3,659,587 | 5/1972 | Baldwin ............... 128/764 |
| 4,166,450 | 9/1979 | Abramson ............. 128/764 |
| 4,312,362 | 1/1982 | Kaufman .............. 128/763 |
| 4,512,766 | 4/1985 | Vailancourt .......... 128/764 |

FOREIGN PATENT DOCUMENTS

| | | |
|---|---|---|
| 0077441 | 4/1983 | European Pat. Off. . |
| 0150127 | 7/1985 | European Pat. Off. . |
| 0045863 | 2/1982 | Fed. Rep. of Germany . |
| 0107578 | 5/1984 | France . |
| 2153012 | 8/1985 | United Kingdom . |

Primary Examiner—Max Hindenburg
Attorney, Agent, or Firm—Ladas & Parry

[57] ABSTRACT

The novel safety blood withdrawal device includes as principal components a syringe body (SK) with a cannula holder, a collecting container (AB) which can be pressed into the syringe body, and a continuous tube (R).

The collecting container is present in the form of a hollow cylinder (11) with a forwardly fitted, fixed sealing plug (12) of elastic material and with an internally fitted sealing piston (13), which is movable relative to the piston inner wall.

The syringe body exhibits at its rear end gripping lugs (21) and at the end face (22) a cannula holder (23).

The continuous tube is mounted by means of a closing piece (31) in a closure block (32) to be movable in the direction of the longitudinal axis of the device, the closure block (32) being tightly secured at the front sealing surface (22) and creating a liquid-conducting connection between the interior space of the cannula and the interior cavity (33) of the closure block (32), and the closing piece (31) tightly fixed to the continuous tube, in the event of pressure on the tube in the direction of the tip of the device, creating a liquid-conducting connection between the interior space of the tube and the interior cavity (33), and, in the event of tension on the continuous tube, sealing this connection in a liquid-tight manner.

The novel device is used, advantageously as a set, for the withdrawal of blood from humans.

8 Claims, 3 Drawing Sheets

U.S. Patent  Dec. 13, 1988  Sheet 1 of 3  4,790,330

BLOOD WITHDRAWAL DEVICE WITH SAFETY VALVE AND CYLINDRICAL CONTAINER

The invention described below relates to a safe blood withdrawal device with a container flask in the form of a syringe, which can be operated and controlled with one hand and into which, for the purpose of operation, in each instance a single-use sealed cylinder is pressed, which after withdrawal of the blood serves at the same time as its container.

Blood withdrawal devices have been known for a long period of time; however, since, according to statements made by experts, the taking of blood samples will increase as a part of diagnostic procedures, there is certainly a requirement for safe blood withdrawal devices which can be operated in a simple manner and which can be produced and stored under conditions free from objection from the hygienic point of view.

The prior art with regard to devices of this type can be divided into two groups: blood withdrawal syringes, in which the pressure adaptation required in order to withdraw blood from veins, or the reduced pressure, is generated by manual displacement of a piston in a cylinder, and devices in which the said reduced pressure is created with the application of evacuated containers or of an emptied rubber bulb.

The first group of apparatuses of this type ares well presented by the invention according to the European Patent Application under publication No. 0 107 578. By means of a piston moved manually in a rearward direction, a reduced pressure is generated in the syringe body, which reduced pressure brings about a situation in which blood is drawn through the cannula, which is connected in front, into the container tube fitted between the cannula and the syringe body. There is no safety arrangement with regard to re-expulsion of the blood, and the device is apparently taken apart for every new blood withdrawal.

The invention according to the European Patent Application under publication No. 0 150 127 also basically belongs to this group of devices: by pressing in the hollow piston into the syringe body, there is generated in the hollow cylinder itself, by the displacement of a sliding piston fitted therein, a reduced pressure which serves to fill with liquid a container vessel which is fitted for practical purposes at the cannula.

The disadvantages of such devices are firstly the inadequate protection against expulsion of the liquid during or after withdrawal and, in the case of blood withdrawal syringes operated with two hands, the impossibility of keeping one hand free for holding, for example, the arm of the patient steady. In the case of the device according to the European Patent Application under publication No. 0 150 127, reference should also be made to the position of the container: the level of the liquid contained therein is at all events lower than the hydrostatic point of the reduced pressure line. It is not clearly evident how the withdrawal of blood can in practice be carried out with this syringe.

Figure 3:
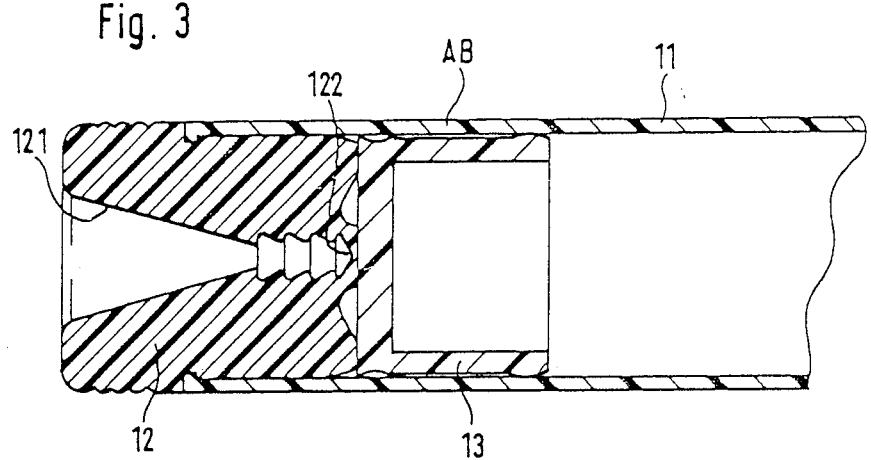

The second group of such devices according to the prior art is represented, inter alia, by the invention according to the European Patent Application under publication No. 0 077 441, specifically in FIGS. 1 and 3: a holder exhibits on both sides needles, one of which is used as the actual cannula, while the other is used for the fastening of a pre-evacuated collecting container to be fitted at the rear. The European Patent Application under publication No. 0 045 863 teaches, in place of an evacuated container, a rubber bulb, which is in each instance emptied and in the course of blood withdrawal serves for the generation of the reduced pressure in the container which is pressed on and which is connected therebetween.

The disadvantages of such systems are the sudden and virtually uncontrolled action of relatively great reduced pressure, which can lead to collapse of the veins. Moreover, the storage life of pre-evacuated containers is limited, and this life is in the first instance still affected by uncertainty to some extent. Finally, none of the apparatuses exhibits any form of protection against re-expulsion.

The currently described blood withdrawal device according to the invention circumvents the aforesaid difficulties and disadvantages by means of new specific properties of construction and arrangement. Above all, the blood withdrawal device according to the invention comes in practice very close to the ideal with regard to contamination, i.e. the once-only use of a device for a withdrawal of blood. The components which are employed repeatedly and which come into contact with the blood can all be constructed of special steel, or of specifically surface-treated steel.

The expressions "front" and "rear" used in this specification in connection with blood withdrawal devices relate to the conventional mode of application of such devices: "front" refers to the direction of the cannula or of the puncture, while "rear" refers to the opposite end of the apparatus in the direction of its longitudinal axis.

This invention specifically relates to a safe blood withdrawal device, which comprises as principal component a syringe body SK with a cannula holder, a collecting container AB which can be pressed into the syringe body, and a continuous tube R. The device is characterized in that the collecting container is present in the form of a hollow cylinder 11 with a forwardly fitted, fixed seal 12 of elastic material, with an internally fitted sealing piston 13 movable relative to the inner wall of the cylinder, and with an opening 14, which is provided at the rear and which permits air to pass out on pressing in the hollow cylinder into the syringe body with displacement of the sealing piston, in that the syringe body exhibits at its rear end gripping lugs 21, which are held in the event of the use of the device, for example, by means of the index and middle fingers, and at the front end face 22 a cannula holder 23, as well as in that the syringe body is constructed to be open at the rear end, and in that the continuous tube is mounted by means of a closing piece 31 in a closure block 32 to be movable in the direction of the longitudinal axis of the device, the closure block 32 being tightly secured at the end face 22 and creating a liquid-conducting connection between the interior space of the cannula and the interior cavity 33 of the closure block 32, and the closing piece 31 tightly fixed to the continuous tube, in the event of pressure on the tube in the direction of the tip of the device, creating a liquid-conducting connection between the interior space of the tube and the interior cavity 33, and, in the event of tension on the continuous tube, sealing this connection in a liquid-tight manner.

The novel blood withdrawal device preferably exhibits a collecting container of injection-moulded polyolefin material as well as a seal 12 in the form of a plug of synthetic or natural rubber which can be made under sterile conditions. This seal shows a depression 121 corresponding to the position of the continuous tube and a thin position 122 for guiding the tube and for determining the place of penetration, the said seal projecting beyond the front end of the collecting container and at the same time serving for the non-sealing guiding of this container in the syringe body. Likewise, there is disposed in this collecting container an internal, movable sealing piston 13, which is likewise injection-moulded from polyolefins and which in its external diameter and in its bearing surface is adapted to the collecting container in such a manner that it forms a seal at the pressure differences occurring for the liquids which are usually to be received. Moreover, the collecting container is constructed in such a manner that—whether empty or filled—it can be placed on the rear closing surface; there is accordingly no need for it to be located.

The same blood withdrawal device preferably exhibits a syringe body of polyolefin material, which body is pressure-formed, and it contains a cannula holder 23 which is integrated in terms of material and shape. Moreover, the cannula can be a steel cannula or a steel tip with an elastic supply line to the cannula holder.

Furthermore, the currently described blood withdrawal device is such a device which includes a continuous tube of special steel, which tube exhibits at the front a closing piece 31, predominantly constructed of injection-moulded acrylic plastics, which establishes or interrupts the liquid-conducting connection from the interior space of the tube to the interior cavity 32 of the closure block and is fitted sealingly and removably to the end of the tube.

This small steel tube is mounted by means of the closing piece 31 in the closure block 32 to be axially movable, the closure block being secured, for example, cemented, at the front, for example, internally at the end face 22 of the syringe body, and creating the liquid-conducting connection between the interior space of the cannula and—in the event of pressure on the continuous tube—its interior cavity 33.

The said closing piece 31—and thus the tube—are mounted to be movable in the axial direction in a liquid-tight manner in the said cavity 33. At the rear, the continuous tube is cut away obliquely, in order in this manner, when the device is used, to facilitate the penetration of the said tube into the thin position 122 of the seal 12.

The blood withdrawal device according to the invention is advantageously available in the form of a set. Therein are packed both the syringe body together with the continuous tube secured therein and also the collecting container or collecting containers. Specifically, in the said set the syringe body together with the continuous tube can be mounted in a separate compartment, which compartment can easily—for example by tearing off—be separated from the remainder of the set container, while the collecting container or collecting containers is (are) mounted together in a second compartment, which second compartment, moreover, after separation of the separate compartment together with the used syringe body, can be labelled and despatched.

The safe blood withdrawal device according to the invention is used for the withdrawal of blood from humans. Such use can, for example, comprise the following steps:
  introduction of the cannula, which is in the first instance fitted rigidly or movably to the blood withdrawal device, into the vein,
  pressing of a collecting container into the syringe body, in the course of which the continuous tube penetrates the front seal 12 of elastic material and presses the inner, movable sealing piston 13 in the collecting container in a rearward direction and thus generates a reduced pressure therein, which reduced pressure, since by the pressure on the tube in the direction of the tip of the device the closing piece 31 is pressed in a forward direction and thus the cannula—interior space 33—tube connection is created, effects the suction of blood into the collecting container, and
  withdrawal of the collecting container on reaching the desired quantity of blood in the collecting container, whereby both the inflow and outflow of blood are stopped, and whereby, in the case of the complete withdrawal of the collecting container, a hermetically sealed container containing the blood withdrawn is obtained.

In the case of the said mode of application, the actual withdrawal of the blood can be carried out repeatedly with the same penetrated cannula, with the same syringe body and continuous tube, successively with the use of various collecting containers, for example with the use of the above described set.

The distinctive features as compared with the prior art will now also be clearly evident from the above general and specific presentations of this invention.

With specific reference to the European Patent Application under publication No. 0 150 127, in which a device which can be operated with one hand—in the form of a syringe—for the generation of reduced pressure is described, which device is suitable, inter alia, also for the withdrawal of blood and for the collection of the same in a separately fitted container, the following should be stated: in that device, the liquid drawn in should never enter the actual body of the device, and above all should not enter the hollow piston which is required for the generation of the reduced pressure and which is pressed into the syringe body. This piston belongs to the device; it is pressed in on every operation of the same. After the withdrawal of the liquid—without any protection whatsoever—the separate container is removed and the piston is withdrawn again from the syringe body, whereby the variable volume producing the reduced pressure in the said piston decreases again to virtually zero.

Likewise, in connection with this publication it should be stated that no statements are made with regard to the materials or substances to be employed in practice in each instance in implementation of the invention and the production or processing methods of the same. However, this is of critical importance in such devices.

On the other hand, the blood withdrawal device according to the invention exhibits a hollow cylinder which is designed as a blood receiver and container and which accordingly is to be used only once. Likewise, the axial small passage tube at the tip of the device is provided with a sealing device, which seal on pressing in the cylinder, i.e. on generating the reduced pressure, automatically opens, and on withdrawal of the container cylinder closes in a liquid-tight manner.

The blood withdrawal device according to the invention is designed, in terms of material and production, in such a manner that it—or its components—can be made under sterile conditions with the usual measures.

The safety blood withdrawal device according to the invention and application thereof will now be explained in detail below, with reference to the attached FIGS. 1 to 4.

The said figures represent only an—albeit preferred—embodiment of the device according to the invention. The inventive concept characterized in the patent claims can also be implemented in other ways by a person skilled in the art.

Figure 2:
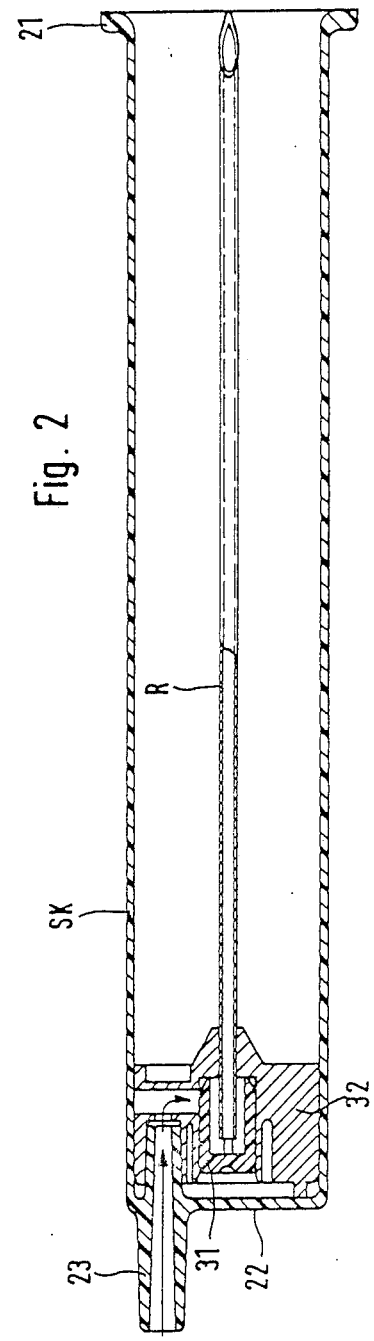
Figure 4A:
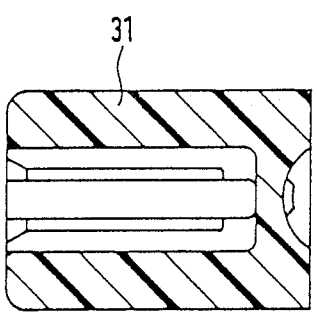
Figure 4B:
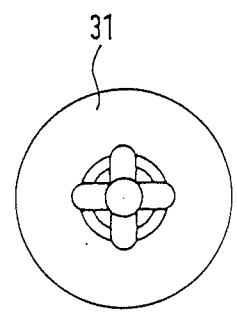

In the drawings:

FIG. 1 shows a central longitudinal section through a blood withdrawal device according to the invention, after completion of the withdrawal of blood (the blood has not been shown); SK is the syringe body, AB the collecting container and R the continuous tube, FIG. 2 shows the corresponding section through the syringe body SK when the continuous tube R has been inserted, without a collecting container pressed in, FIG. 3 shows a central longitudinal section through the front part of the collecting container AB which has not yet been pressed in, and FIGS. 4a and 4b show central longitudinal and transverse sections respectively through the closing piece 31 secured at the front at the continuous tube.

Figure 5:
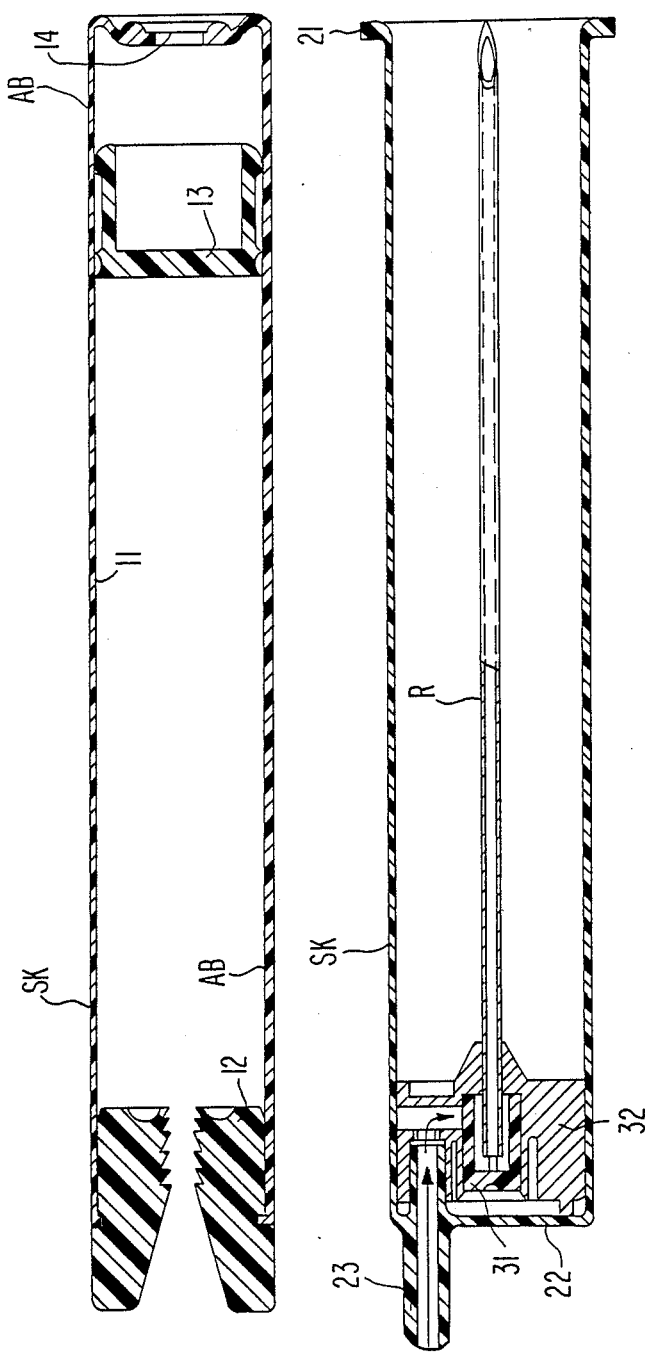

FIG. 5 shows a blood withdrawal device according to the invention formed as a kit.

As regards the actual withdrawal of the blood, three sections are to be distinguished. In the following description of the same, it is assumed that the blood withdrawal device is present in the form of the set which has already been mentioned above, i.e. in a pack in which a separable compartment contains the syringe body SK together with the used continuous tube and possibly the cannula, and a second compartment contains the collecting container or collecting containers; all parts are pretreated under sterile conditions and possibly even individually packed.

In the first instance—after the necessary hygienic and bacteriological preparations—the cannula is fitted to the syringe body and then inserted into the vein of the patient. In the case of the fixed securing of the cannula on the syringe body SK, the latter is itself employed for penetration; in the event of the use of perfusion instruments, their hose connection is placed on the cannula holder 23, the cannula is inserted into the vein and fixed to the skin by means of the securing stickers.

The syringe body is now present in the basic form according to FIG. 2; the continuous tube R is axially mounted by means of closing piece 31 in the closure block 32, in the syringe body SK with gripping lugs 21 (only schematically shown in FIGS. 1 and 2), end face 22 and with an integrated cannula holder 23, all injection-moulded from a polyolefin material.

The tube R consists of stainless special steel and is obliquely cut at the rear. It is fixedly secured in the closing piece 31, i.e. in the case of the conventional application of the device the said closing piece does not move in relation to the tube. At the rear, the end of the tube is approximately flush with the end of the syringe body.

The closing piece 31 is designed in such a manner that liquid, specifically blood, can always pass from within the said piece to the interior space of the continuous tube. This is clearly evident from FIGS. 4a and 4b.

The closing piece 31 is mounted to be axially displaceable—but liquid-tight—in the closure block 32. In the arrangement represented in FIG. 2, the closing piece is arranged to be drawn in a rearward direction, i.e. the liquid-conducting connection from the interior space of the cannula holder and the interior cavity 33 of the closure block 32 to the interior space of the closing piece 31 is interrupted. The closing piece 31 consists, for example, of injection-moulded polyacrylate and is stretched onto or thermally fitted to the tube R.

The closure block 32 consists of the same material as or of a similar material to the syringe body, and is also produced in a similar manner. It is fixed, at the front, in the syringe body, e.g. by clamping or adhesion, and forms a seal at the interior walls of the syringe body. Liquid, specifically blood, can only pass on the path indicated by means of an arrow in FIG. 2 to the closing piece 31 and thus into the continuous tube.

Secondly, a collecting container AB is now handed over and, where appropriate, unpacked. This is present in the basic form according to FIG. 3, i.e. the seal 12 is fixed, at the front, at the hollow piston 11 and projects beyond the latter. The sealing piston 13 is likewise disposed at the front, abutting against the seal. The collecting containers are supplied in this practically invariable arrangement.

The collecting container is now pressed, in the condition in which it is present and, where appropriate, after the removal of packaging, from behind into the syringe body. In the course of this, the obliquely cut tube end is guided through the depression 121, which is specifically designed for this purpose, to the weakened position 122 in the seal 12, and penetrates the latter with the action of sufficient pressure. When the tube end has passed through the seal 12, under the further action of pressure on the collecting container, the tube end presses the sealing piston 13 in the hollow cylinder 11 in a rearward direction and thus generates a reduced pressure in the increasing volume between the seal 12 and the piston 13. As a result of the pressure exercised in the course of this in the direction of the tip of the device on the continuous tube (because of the adhesion forces between the elastic seal and the tube), the tube together with the closing piece 31 is pressed in a forward direction, and there is thus opened the liquid-conducting connection from the internal space of the cannula via the cavity 33 of the closure block 31—conduits in the closing piece—continuous tube into the space in the collecting container AB between the seal 12 and the piston 13. The latter thus fills to the desired level, which is achieved in a simple manner by means of the pressure exerted on the collecting container. In this manner, the rate of withdrawal of the blood can also be regulated in an extremely simple manner.

The hollow cylinder 11 advantageously likewise consists of injection-moulded polyolefins, as does also the piston 13. The latter is designed in such a manner that, as a result of the action of the pressure difference reached in the case of the conventional application of the device according to the invention, it is moved relatively easily in the direction of the longitudinal axis, and however, in the course of this, forms a seal between itself and the interior wall of the hollow cylinder 11 with respect to liquids—e.g. by means of the two sealing rings indicated in FIG. 3.

The condition of the device according to the invention at the conclusion of the withdrawal of blood is essentially represented in FIG. 1: the collecting container AB has been pressed as far as the abutment of the seal in the form of the sealing plug 12 at the closure block 31 into the syringe body SK. In this manner, the maximum possible quantity of blood (not shown) has been withdrawn.

The fixed sealing plug 12, to be penetrated by means of the continuous tube, consists of a natural or synthetic rubber; it is essential that this material just like all other materials used in the device—can be made under sterile conditions in conventional devices.

The collecting container employed can, where appropriate, include the usual means for the preservation and/or conversion of the blood withdrawn.

As soon as the desired quantity of blood is present, the collecting container AB—thirdly—is removed again in a rearward direction from the syringe body.

In the course of this, two events take place: as a result of tension action on the tube in the direction of the rear end of the device, the continuous tube and also the closing part 31 are moved in a rearward direction, and the liquid-conducting connection between on the one hand the interior space of the cannula and the interior cavity 33 of the closure block 32 and on the other hand interior conduits of the closing part 31 and the tube is interrupted. The possibility of expelling blood again through the cannula does not exist.

Finally, in the course of the further withdrawal of the collecting container, the continuous tube is also drawn out of the plug 12, which, because it consists of elastic material, subsequently forms a tight seal.

The sections 2 and 3 of the described withdrawal of blood can clearly be carried out as frequently as is desired, with the use of the same inserted cannula and syringe body, plus the continuous tube.

Following the completion of the withdrawal of blood—in the event of the use of a set—the filled collecting container is replaced in each instance in its compartment in the packaging, the cannula is correctly pulled out again and put away, together with the syringe body with the continuous tube, in the separable compartment of the packaging, the last mentioned compartment is separated from the remainder of the set (for example by tearing off), and the remainder of the set is labelled and, where appropriate, despatched.

We claim:

1. A blood withdrawal device comprising:
    a syringe body having a front end and a rear end, a hollow cannula holder extending forwardly from the front end, a closure block fixedly mounted in the syringe body at the front end thereof, the closure block defining an interior cavity therein, a closing piece mounted in the interior cavity of the closure block and movable therein between a first open position and a second closed position, a hollow tube member having front and rear ends, the front end of the tube member being fixedly mounted in the closing piece and movable therewith between the first and second positions, the first open position of the closing piece permitting the flow of blood from the cannula holder to the interior cavity of the closure block to the closing piece and interior of the hollow tube member, the second closed position preventing flow of blood from the cannula holder through the closing piece; and
    a collecting container comprising a hollow cylinder having a front end and a rear end, the collecting container capable of being slidably received within the syringe body, the collecting container comprising a seal at its front end through which the tube member may pass in a sealing arrangement, a piston movable within the hollow cylinder and in sealing engagement therewith, and an opening at the rear end of the collecting container which is sealed by the abutment of the piston thereagainst,
    wherein insertion of the collecting container into the syringe body moves the tube member and the closing piece into the first open position, further insertion causes the piston to move from the front end of the collecting container to the rear end thereof thus creating a negative pressure differential permitting blood to flow from the cannula holder to the collecting container, and, upon withdrawal of the collecting container, the closing piece is moved into the second closed position to prevent flow of blood from the cannula holder to the tube member.

2. A device as claimed in claim 1 wherein the hollow cylinder of the collecting container comprises injection-moulded polyolefin material, the seal comprises a rubber plug and comprises a depression at the position of penetration by the tube member, and a weakened portion for guiding the tube member to accurately penetrate the seal.

3. A device as claimed in claim 2 wherein the seal projects beyond the front end of the collecting container, and moves through the syringe in non-sealing engagement therewith.

4. A device as claimed in claim 3 wherein the piston is formed from injection-moulded polyolefins.

5. A device as claimed in claim 1 wherein the syringe body is compression-moulded from polyolefin material and has an integrated cannula holder, the cannula holder receiving a cannula and supply line thereto.

6. A device as claimed in claim 1 wherein the tube member is comprised of steel and is sealingly and fixedly attached to the closure piece, and the rear end of the tube member is obliquely cut to provide a sharpened point to facilitate penetration of the tube member into the seal.

7. A device as claimed in claim 1 comprising a syringe body and collecting container packed as a kit.

8. A device as claimed in claim 7 wherein the kit comprises a housing of at least two compartments, the syringe body being coated in the first compartment and at least one collecting container being located in a second compartment.

* * * * *